United States Patent [19]

Winter et al.

[11] 4,234,585
[45] Nov. 18, 1980

[54] 1,2-DIHYDROQUINOLINE-2-ONE DERIVATIVES

[75] Inventors: Werner Winter, Heppenheim; Walter-Gunar Friebe, Darmstadt; Wolfgang Kampe, Heddesheim; Androniki Roesch, Mannheim; Otto-Henning Wilhelms, Weinheim-Rittenweier, all of Fed. Rep. of Germany

[73] Assignee: Boehringer Mannheim GmbH, Mannheim, Fed. Rep. of Germany

[21] Appl. No.: 45,472

[22] Filed: Jun. 4, 1979

[30] Foreign Application Priority Data

Jun. 23, 1978 [DE] Fed. Rep. of Germany ....... 2827566

[51] Int. Cl.$^3$ .................... A61K 31/495; C07D 401/12
[52] U.S. Cl. ...................................... 424/250; 544/363
[58] Field of Search .......................... 544/363; 424/250

[56] References Cited

FOREIGN PATENT DOCUMENTS 1932384 1/1970 Fed. Rep. of Germany ........... 544/363

*Primary Examiner*—Paul M. Coughlan, Jr.
*Attorney, Agent, or Firm*—Sprung, Felfe, Horn, Lynch & Kramer

[57] ABSTRACT

A (4-substituted-piperazin-1-yl)-alkoxy-2-oxo-1,2-dihydroquinoline of the formula:

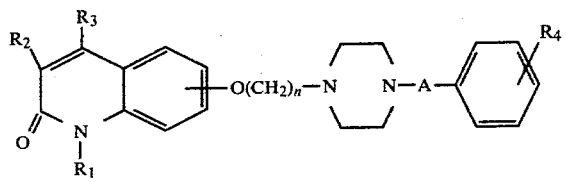

(I)

in which
  $R_1$, $R_2$ and $R_3$ each independently is hydrogen or a lower alkyl radical,
  $R_4$ is hydrogen, halogen, or a lower alkyl or lower alkoxy radical,
  n is 2, 3, 4 or 5 and
  A is a valency bond or a methylene radical optionally substituted by a phenyl radical, or a salt thereof, which exhibits anti-allergic and anti-hypertensive activity.

9 Claims, No Drawings

1,2-DIHYDROQUINOLINE-2-ONE DERIVATIVES

The present invention is concerned with new 1,2-dihydroquinolin-2-one derivatives and with the preparation thereof, as well as with pharmaceutical compositions containing these derivatives.

The 1,2-dihydroquinolin-2-ones according to the present invention are compounds of the general formula:

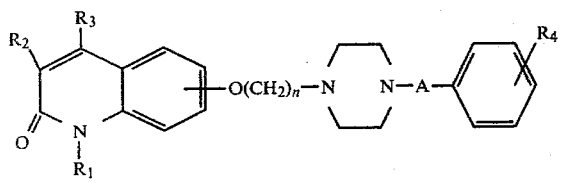

(I)

wherein $R_1$, $R_2$ and $R_3$, which can be the same or different, are hydrogen atoms or lower alkyl radicals, $R_4$ is a hydrogen or halogen atom or a lower alkyl or lower alkoxy radical, n is 2, 3, 4 or 5 and A is a valency bond or a methylene radical optionally substituted by a phenyl radical; and the pharmacologically acceptable salts thereof with non-toxic inorganic and organic acids.

The lower alkyl radicals in the definitions of $R_1$, $R_2$ and $R_3$ and the lower alkyl and lower alkoxy radicals in the definition of $R_4$ can be straight-chained or branched and contain up to 6 and preferably up to 4 carbon atoms.

The halogen atom is preferably a fluorine, chlorine or bromine atom, chlorine being most preferred.

We have found that the new basic ethers of 1,2-dihydroquinolin-2-one of general formula (I), in the case of parenteral as well as per oral administration, exhibit an outstanding anti-allergic action which can be demonstrated in the pharmacological test of passive cutaneous anaphylaxis (PCA test) in vivo in rats. The inhibiting potency of this group of compounds can also be convincingly demonstrated in vitro on the basis of the antigen-induced mast cell degranulation. Therefore, the compounds of general formula (I) according to the present invention can be used especially advantageously for combating allergic diseases, for example allergic asthma, hay fever and urticaria.

The new compounds of general formula (I) can be further worked up in various ways to give compounds which also display pharmacological effectiveness, especially anti-allergic and anti-hypertensive effectiveness. Therefore, they are also valuable intermediates for the preparation of pharmacologically-effective materials.

The new compounds (I) according to the present invention can be prepared in various ways. Thus, for example:

(a) a 1,2-dihydroquinolin-2-one of the general formula:

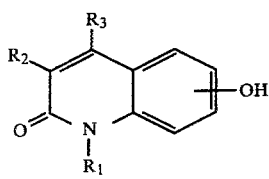

(II)

wherein $R_1$, $R_2$ and $R_3$ have the same meanings as above, is reacted with a piperazine derivative of the general formula:

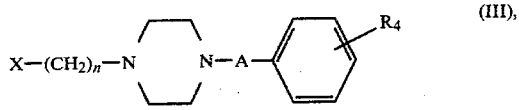

(III), wherein n, A and $R_4$ have the same meanings as above and X is a reactive residue; or (b) a 1,2-dihydroquinolin-2-one of the general formula:

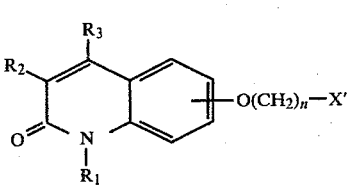

(IV), wherein $R_1$, $R_2$, $R_3$ and n have the same meanings as above and X' is a reactive residue, is reacted with a piperazine derivative of the general formula:

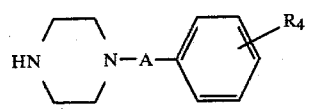

(V), wherein A and $R_4$ have the same meanings as above, and, when $R_1$ is a hydrogen atom in the product obtained, the product is, if desired, subsequently N-alkylated and, if desired, a compound obtained of general formula (I) is converted into a pharmacologically acceptable salt.

The reactive residues X and X' can be any known group which can be nucleophilically removed. Especially preferred residues of this type include chlorine and bromine atoms, as well as mesyloxy and tosyloxy radicals.

The reactions according to the present invention can be carried out by known methods. Thus, for example, in the case of process (a), the hydroxy-1,2dihydroquinolin-2-one of general formula (II) is condensed in an appropriate solvent, such as ethanol, isopropanol or preferably ethoxyethanol, with the piperazine of general formula (III) at an elevated temperature, in the presence of an alkali alcoholate. As solvent, there can also be used dimethylformamide, dimethyl sulphoxide or hexametapol.

In the case of process (b), the reaction of a dihydroquinolin-2-one of general formula (IV) with a piperazine of general formula (V) is carried out in one of the above-mentioned solvents, advantageously with the addition of a tertiary amine, such as triethylamine, or of a Huenig base or of a strongly basic ion exchanger but can also be carried out with, for example, potassium tert.-butylate in dimethyl sulphoxide.

The starting materials of general formula (II), (III), (IV) and (V) are either known from the literature or can be prepared analogously to the processes known from the literature.

The pharmacologically acceptable salts are obtained in the conventional manner, for example by neutralization of the compounds of general formula (I) with non-toxic inorganic or organic acids, for example hydrochloric acid, sulphuric acid, phosphoric acid, hydrobromic acid, acetic acid, lactic acid, citric acid, malic acid, salicylic acid, malonic acid, maleic acid or succinic acid.

For the preparation of pharmaceutical compositions, the compounds of general formula (I) are mixed in the usual way with appropriate pharmaceutical carrier substances and aroma, flavoring and coloring materials and formed, for example, into tablets or dragees or, with the addition of appropriate adjuvants, suspended or dissolved in water or in an oil, for example olive oil.

The compounds of general formula (I) can be administered orally and parenterally in liquid or solid form. As injection medium, it is preferred to use water which contains the stabilizing agents, solubilizing agents and/or buffers conventionally used for injection solutions. Additives of this type include, for example, tartrate and borate buffers, ethanol, dimethyl sulphoxide, complex formers (such as ethylendiamine-tetraacetic acid), high molecular weight polymers (such as liquid polyethylene oxide) for viscosity regulation and polyethylene derivatives of sorbitol anhydrides.

Solid carrier materials which can be used include, for example, starch, lactose, mannitol, methyl cellulose, talc, highly dispersed silicic acid and high molecular weight polymers (such as polyethylene glycol).

Compositions suitable for oral administration can, if desired, contain flavoring and/or sweetening agents. For topical administration, the compounds (I) according to the present invention can also be used in the form of powders or salves, for which purpose they are mixed with, for example, powdered, physiologically compatible diluents or conventional salve bases.

Apart from the compounds mentioned in the specific examples, the following compounds are also preferred according to the present invention:
4-methyl-6-{2-[4-(4-chlorobenzyl)-piperazin-1-yl]-ethoxy}-2oxo-1,2-dihydroquinoline;
4-methyl-8-{3-[4-(4-chlorobenzyl)-piperazin-1-yl]-propoxy}-2-oxo-1,2-dihydroquinoline; and
1,4-dimethyl-8{3-[4-(4-chlorobenzyl)-piperazin-1-yl]-propoxy}-2-oxo-1,2-dihydroquinoline.

The following examples are given for the purpose of illustrating the present invention, the structure of the compounds given therein having been ascertained by CHN analysis and by IR, UV, NMR and mass spectra.

EXAMPLE 1

4-Methyl-7-{3-[4-(4-chlorobenzyl)-piperazin-1-yl]propoxy}-2-oxo-1,2-dihydroquinoline.

2.3 g. (0.1 mol) Sodium are dissolved in 320 ml. ethoxyethanol and subsequently mixed with 17.5 g. (0.1 mol) 4-methyl-7-hydroxy-2-oxo-1,2-dihydroquinoline. The reaction mixture is then stirred for 15 minutes, whereafter 31.6 g. (0.11 mol) 3-[4-(4-chlorobenzyl)-piperazin-1-yl]-propyl chloride in 30 ml. ethoxyethanol are added dropwise thereto, followed by heating to 90° C. for 10 hours. The solvent is then substantially removed in a vacuum. The residue is mixed with water, extracted with methylene chloride and the organic phase dried and then evaporated. The evaporation residue is purified by stirring with diethyl ether. There are obtained 22.9 g. (53.8% of theory) 4-methyl-7-{3-[4-(4-chlorobenzyl)-piperazin-1-yl]-propoxy}-2-oxo-1,2-dihydroquinoline; m.p. 170°–171° C.

The base is dissolved in methylene chloride and some methanol and, by the addition of ethereal hydrochloric acid and subsequent dilution with diethyl ether, the corresponding dihydrochloride is precipitated out; m.p. 271°–272° C.

EXAMPLE 2

3,4-Dimethyl-7-{3-[4-(4-chlorobenzyl)-piperazin-1-yl]-propoxy}-2-oxo-1,2-dihydroquinoline.

From 9.46 g. (0.05 mol) 3,4-Dimethyl-7-hydroxy-2-oxo-1,2-dihydroquinoline and 15.8 g. (0.055 mol) 3-[4-(4-chlorobenzyl)-piperazin-1-yl]-propyl chloride, in the manner described in Example 1, there are obtained 12.8 g. (58.2% of theory) 3,4-dimethyl-7-{3-[4-(4-chlorobenzyl)-piperazin-1-yl]-propoxy}-2-oxo-1,2-dihydroquinoline; m.p. 143°–144° C. The corresponding dihydrochloride, which has a water content of 4.2%, melts at 273°–274° C.

EXAMPLE 3

1,4-Dimethyl-7-{3-[4-(4-chlorobenzyl)-piperazin-1-yl]-propoxy}-2-oxo-1,2-dihydroquinoline.

From 9.46 g. 1,4-Dimethyl-7-hydroxy-2-oxo-1,2-dihydroquinoline and 15.8 g. 3-[4-(4-chlorobenzyl)-piperazin-1-yl]-propyl chloride, in the manner described in Example 1, there are obtained 15.2 g. (63.8% of theory) 1,4-dimethyl-7-{3-[4-(4-chlorobenzyl)-piperazin-1-yl]-propoxy}-2-oxo-1,2-dihydroquinoline monohydrochloride. Thermoanalysis shows a melting point of 189° C. The corresponding dihydrochloride melts at 260°–263° C.

EXAMPLE 4

4-Methyl-7-{3-[4-(3-chlorophenyl)-piperazin-1-yl]-propoxy}-2-oxo-1,2-dihydroquinoline.

In a manner analogous to that described in Example 1, from 8.76 g. (0.05 mol) of 4-methyl-7-hydroxy-2-oxo-1,2-dihydroquinoline and 15 g. (0.055 mol) 3-[4-(3-chlorophenyl)-piperazin-1-yl]-propyl chloride, as well as 1.55 g. (0.05 mol) sodium in 160 ml. ethoxyethanol, after a 5 hour reaction period at 90° C., there are obtained 10.5 g. (51% of theory) 4-methyl-7-{3-[4-(3-chlorophenyl)-piperazin-1-yl]-propoxy}-2-oxo-1,2-dihydroquinoline; m.p. 212°–214° C.

EXAMPLE 5

4-Methyl-6-{3-[4-(4-chlorobenzyl)-piperazin-1-yl]-propoxy}-2-oxo-1,2-dihydroquinoline.

0.69 g. (0.03 mol) Sodium is dissolved in 75 ml. isopropanol, mixed with 4.89 g. (0.03 mol) 4-methyl-6-hydroxy-2-oxo-1,2-dihydroquinoline and stirred for 10 minutes at ambient temperature. After the addition of 9.5 g. (0.033 mol) 3-[4-(4-chlorobenzyl)-piperazin-1-yl]-propyl chloride in 25 ml. isopropanol, the reaction mixture is boiled for 16 hours. Thereafter, it is evaporated in a vacuum and the residue is taken up in methylene chloride and shaken up with 1 N aqueous sodium hydroxide solution. The organic phase is then separated off, dried and evaporated and the evaporation residue triturated with diethyl ether, the solid product obtained then being recrystallized from ethanol. There are obtained 6.25 g. (49% of theory) 4-methyl-6-{3-[4-(4-chlorobenzyl)-piperazin-1-yl]-propoxy}-2-oxo-1,2-dihydroquinoline; m.p. 195°–197° C.

EXAMPLE 6

4-Methyl-6-{3-[4-(4-fluorobenzyl)-piperazin-1-yl]-propoxy}-2-oxo-1,2-dihydroquinoline.

In a manner analogous to that described in Example 5, by the appropriate reaction of 4-methyl-6-hydroxy-2-oxo-1,2-dihydroquinoline with 3-[4-(4-fluorobenzyl)-piperazin-1-yl]-propyl chloride, there is obtained 4-methyl-6-{3-[4-(4-fluorobenzyl)-piperazin-1-yl]-propoxy}-2-oxo-1,2-dihydroquinoline which, after recrystallization from ethanol, melts at 178°–180° C.

EXAMPLE 7

4-Methyl-6-{3-[4-(4-tert.-butyl-benzyl)-piperazin-1-yl]-propoxy}-2-oxo-1,2-dihydroquinoline.

In a manner analogous to that described in Example 5, by the reaction of 4-methyl-6-hydroxy-2-oxo-1,2-dihydroquinoline with 3-[4-(4-tert.-butylbenzyl)-piperazin-1-yl]-propyl chloride, there is obtained 4-methyl-6-{3-[4-(4-tert.-butylbenzyl)-piperazin-1-yl]-propoxy}-2-oxo-1,2-dihydroquinoline which, after recrystallization from ethyl acetate, melts at 171°–172° C.

EXAMPLE 8

4-Methyl-6-{3-[4-(4-methylbenzyl)-piperazin-1-yl]-propoxy}-2-oxo-1,2-dihydroquinoline.

4-Methyl-6-hydroxy-2-oxo-1,2dihydroquinoline is reacted with 3-[4-(4-methylbenzyl)-piperazin-1-yl]-propyl chloride in a manner analogous to that described in Example 5. There is obtained 4-methyl-6-{3-[4-(4-methylbenzyl)-piperazin-1-yl]-propoxy}-2-oxo-1,2-dihydroquinoline which, after recrystallization from diethyl ether, melts at 162°–163° C.

EXAMPLE 9

6-{3-[4-(4-Chlorobenzyl)-piperazin-1-yl]-propoxy}-2-oxo-1,2-dihydroquinoline.

4.8 g. (0.03 mol) 6-hydroxy-2-oxo-1,2-dihydroquinoline are dissolved in 60 ml. water and 30 ml. 1 N aqueous sodium hydroxide solution. The solution is subsequently substantially evaporated and the residue is taken up in 75 ml. dimethylformamide and mixed with 14.3 g. (0.05 mol) 3-[4-(4-chlorobenzyl)-piperazin-1-yl]-propyl chloride. After stirring the reaction mixture for 4 hours at 100° C., the solvent is removed in a vacuum and the residue is taken up in methylene chloride. The solution obtained is shaken up with a 1 N aqueous solution of sodium hydroxide and the organic phase is separated off, dried and evaporated in a vacuum. The evaporation residue is subsequently triturated with ethyl acetate and recrystallized from ethanol. There are obtained 6.3 g. (51% of theory) 6-{3-[4-(4-chlorobenzyl)-piperazin-1-yl]-propoxy}-2-oxo-1,2-dihydroquinoline.

The base has a melting point of 180°–182° C.

EXAMPLE 10

4-Methyl-6-{3-[4-(2-propoxybenzyl)-piperazin-1-yl]-propoxy}-2-oxo-1,2-dihydroquinoline.

In a manner analogous to that described in Example 9, 4-methyl-6-hydroxy-2-oxo-1,2-dihydroquinoline is reacted with 3-[4-(2-propoxybenzyl)-piperazin-1-yl]-propyl chloride. There is obtained 4-methyl-6-{3-[4-(2-propoxybenzyl)-piperazin-1-yl]-propoxy}-2-oxo-1,2-dihydroquinoline in a yield of 53% of theory in the form of an oily base. The corresponding hydrochloride is obtained from an acetone solution of the base, by the addition of ethereal hydrochloric acid, in amorphous fomrm with a melting point of about 140°–145° C.

EXAMPLE 11

1,4-Dimethyl-6-{3-[4-(4-chlorobenzyl)-piperazin-1-yl]-propoxy}-2-oxo-1,2-dihydroquinoline.

1,4-Dimethyl-6-hydroxy-2-oxo-1,2-dihydroquinoline is reacted with 3-[4-(4-chlorobenzyl)-piperazin-1-yl]-propyl chloride in a manner analogous to that described in Example 3. There is obtained 1,4-dimethyl-6-{3-[4-(4-chlorobenzyl)-piperazin-1-yl]-propoxy}-2-oxo-1,2-dihydroquinoline in the form of a hydrochloride which melts, with decomposition, at 215°–220° C.

EXAMPLE 12

4-Methyl-7-{3-[4-(3-methoxybenzyl)-piperazin-1-yl]-propoxy}-2-oxo-1,2-dihydroquinoline.

In a manner analogous to that described in Example 1, 8.76 g. (0.05 mol) of 4-methyl-7-hydroxy-2-oxo-1,2-dihydroquinoline are reacted with 15.5 g. (0.055 mol) 3-[4-(3-methoxybenzyl)-piperazin-1-yl]-propyl chloride in ethoxyethanol by heating for 4 hours at 90° C. After working up the reaction mixture, the crude product obtained is triturated with diethyl ether. There are obtained 12.2 g. (57.9% of theory) 4-methyl-7-{3-[4-(3-methoxybenzyl)-piperazin-1-yl]-propoxy}-2-oxo-1,2-dihydroquinoline; m.p. 149°–150° C. A corresponding hydrochloride melts at 265°–268° C.

EXAMPLE 13

4-Methyl-7-{3-[4-(4-methoxybenzyl)-piperazin-1-yl]-propoxy}-2-oxo-1,2-dihydroquinoline.

In a manner analogous to that described in Example 12 and using 3-[4-(4-methoxybenzyl)-piperazin-1-yl]-propyl chloride, there are obtained 11 g. (52% of theory) 4-methyl-7-{3-[4-(4-methoxybenzyl)-piperazin-1-yl]-propoxy}-2-oxo-1,2-dihydroquinoline; m.p. 167°–168° C. The corresponding dihydrochloride melts at 248°–250° C.

EXAMPLE 14

4-Methyl-7-{3-[4-(2-methoxybenzyl)-piperazin-1-yl]-propoxy}-2-oxo-1,2-dihydroquinoline.

In a manner analogous to that described in Example 12, 8.76 g. (0.05 mol) 4-methyl-7-hydroxy-2-oxo-1,2-dihydroquinoline are reacted for 4 hours at 90° C. with 15.5 g. (0.055 mol) 3-[4-(2-methoxybenzyl)-piperazin-1-yl]-propyl chloride. There are obtained 11.7 g. (55.5% of theory) 4-methyl-7-{3-[4-(2-methoxybenzyl)-piperazin-1-yl]-propoxy}-2-oxo-1,2-dihydroquinoline; m.p. 151°–152° C. The corresponding hydrochloride melts at 265°–266° C.

EXAMPLE 15

4-Methyl-7-[3-(4-benzylpiperazin-1-yl)-propoxy]-2-oxo-1,2-dihydroquinoline.

In a manner analogous to that described in Example 12, 8.76 g. 4-methyl-7-hydroxy-2-oxo-1,2-dihydroquinoline are reacted for 4 hours at 90° C. with 3-(4-benzylpiperazin-1-yl)-propyl chloride. There are obtained 11.4 g. (58.3% of theory) 4-methyl-7-[3-(4-benzylpiperazin-1-yl)-propoxy]-2-oxo-1,2-dihydroquinoline base with a melting point of 185°–186° C. The corresponding hydrochloride melts at 279°–281° C.

EXAMPLE 16

3-n-Butyl-4-methyl-7-{3-[4-(4-chlorobenzyl)-piperazin-1-yl]-propoxy}-2-oxo-1,2dihydroquinoline.

In a manner analogous to that described in Example 1, 3-n-butyl-4-methyl-7-hydroxy-2-oxo-1,2-dihydroquinoline is reacted with 3-[4-(4-chlorobenzyl)-piperazin-1-yl]-propyl chloride in ethoxyethanol. There is obtained 3-n-butyl-4-methyl-7-{3-[4-(4-chlorobenzyl)-piperazin-1-yl]-propoxy}-2-oxo-1,2-dihydroquinoline in a yield of 57.5% of theory; m.p. 148°–149° C.

The same compound is obtained when 7-(3-chloropropoxy)-3-n-butyl-4-methyl-2-oxo-1,2-dihydroquinoline (m.p. 203° C.) is boiled for 8 hours with 4-(4-chlorobenzyl)-piperazine in tetrahydrofuran in the presence of a tertiary base, for example N-ethyl-diisopropylamine.

EXAMPLE 17

4-Methyl-7-{3-[4-(diphenylmethyl)-piperazin-1-yl]-propoxy}-2-oxo-1,2-dihydroquinoline.

In a manner analogous to that described in Example 1, 8.76 g. 4-methyl-7-hydroxy-2-oxo-1,2-dihydroquinoline are reacted with 18.1 g. 3-[4-(diphenylmethyl)-piperazin-1-yl]-propyl chloride in ethoxyethanol. There are obtained 15 g. (64% of theory) 4-methyl-7-{3-[4-(diphenylmethyl)-piperazin-1-yl]-propoxy}-2-oxo-1,2-dihydroquinoline base with a melting point of 208°–210° C.

With respect to the proper dosage and methods of application for the instant compounds, these are comparable to those for the commercially known compound "Fragivix", i.e. 2-ethyl-3-(4'-hydroxybenzoyl)-benzofuran. They can also be administered per os. The instant compounds make possible comprehensive therapy of acute as well as chronic phlebological and capillary afflications as well as varicose syndromes. The instant compounds retard reactions leading to edemas and swellings, including those of allergic origin.

The typical daily dosage of 10 to 300 mg results in reducing or eliminating the above afflications, commonly within some days. A preferred dosage is 30–100 mg.

The superior activity of the novel compounds is shown by comparing the inhibition of the passive cutaneous anaphylactic reaction in rats produced by injection of serum containing reaginic antibodies to egg albunin. Diethylcarbamazin, i.e. 1-diethylcarbamoyl-4-methylpiperazine, was used as a comparison compound. Specifically, tests were run as follows:

Serum containing reaginic (IgE-like) antibody to egg albumin was prepared by injecting rats intramuscularly with 0.1 ml of a solution of the antigen (10 mg/ml) in saline together with 0.5 ml of Bordetella pertussis vaccine (Behring; $2 \times 10^{10}$ organisms/ml). 9–14 Days later the animals were bled from the abdominal aorta; the serum was pooled and stored at $-20°$ C. until required. The titer of the serum, i.e. the highest dilution inducing passive cutaneous anaphylaxis (PCA) in the rat following a 48-hour latent period, was between 1:8 and 1:32. For use in these experiments the serum was diluted 1:24. The reaginic nature of the antibody was demonstrated by its ability to induce PCA with a latent period in excess of 7 days and also by abolition of its PCA activity by heating it at 56° C. for 1 hour.

The animals were anesthetized with 2,2-dichloro-1,1-difluoroethyl-methyl ether, sold under the trademark Penthrane, and were sensitized by injecting 0.1 ml of the antiserum into the shaved abdominal flanks. After 48 hours for reaginic PCA, the animals were given an intravenous injection of 1 ml of saline solution containing 0.5% by weight of egg albumin and 0.25% by weight of Evans blue.

After having killed and exsanguinated the animals, the size in square millimeters and the intensity, in arbitrary scores, of the resulting blue spot were determined. The product of these two parameters was used to determine the degree of the reaction and the degree of reaction with no active material was taken as the standard against which to measure % inhibition of the anaphylactic reaction.

6 Animals were used per dose level and for control.

The test materials was administered per os immediately before the antigen. The volume of the application was varied to give the indicated dosage of active material. The results obtained were as follows:

TABLE

PCA Reaction in Rats Induced by Reaginic Antibodies (Ovalbuman 2 × cryst. and Bord. pertussis $2 \times 10^{10}$)

| Active Material | Dose, mg/kg | Inhibition PCA, % |
|---|---|---|
| Diethylcarbamazin | 100 | 47 |
| Example 1 | 1.5 | 35 |
| Example 4 | 3.0 | 28 |
| Example 5 | 3.0 | 32 |
| Example 9 | 3.0 | 20 |
| Example 11 | 3.0 | 17 |
| Example 13 | 3.0 | 20 |
| Example 14 | 3.0 | 23 |
| Example 15 | 3.0 | 34 |
| Example 16 | 3.0 | 35 |

These pharmacological data show that the novel compounds exert a far stronger antianaphylactoid activity than Diethylcarbamazin.

It will be appreciated that the instant specification and examples are set forth by way of illustration and not limitation, and that various modifications and changes may be made without departing from the spirit and scope of the present invention.

What we claim is:

1. A (4-substituted-piperazin-1-yl)-alkoxy-2-oxo-1,2-dihydroquinoline of the formula:

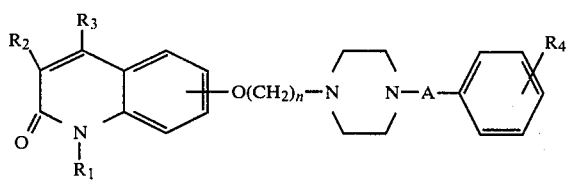

(I)

in which
   $R_1$, $R_2$ and $R_3$ each independently is hydrogen or an alkyl radical with 1 to 6 carbon atoms,
   $R_4$ is hydrogen, halogen, or an alkyl or alkoxy radical with 1 to 6 carbon atoms,
   n is 2, 3, 4 or 5 and
   A is a valency bond or a methylene radical optionally substituted by phenyl,
or a salt thereof with a pharmacologically acceptable acid.

2. A compound or salt thereof according to claim 1, in which

R₁, R₂ and R₃ each independently is hydrogen or alkyl with 1 to 4 carbon atoms, and
R₄ is hydrogen, chlorine, or alkyl or alkoxy with 1 to 4 carbon atoms.

3. A compound or salt thereof according to claim 1, wherein such compound is 4-methyl-7-{3-[4-(4-chlorobenzyl)-piperazin-1-yl]-propoxy}-2-oxo-1,2-dihydroquinoline of the formula

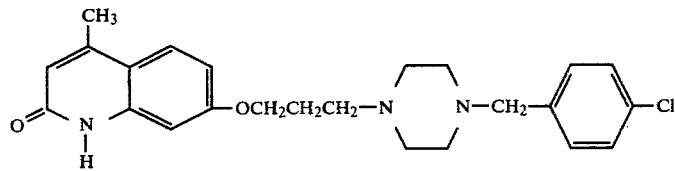

4. A compound or salt thereof according to claim 1, wherein such compound is 4-methyl-6-{3-[4-(4-chlorobenzyl)-piperazin-1-yl]-propoxy}-2-oxo-1,2-dihydroquinoline of the formula

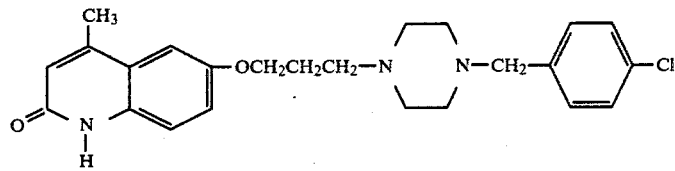

5. A compound or salt thereof according to claim 1, wherein such compound is 4-methyl-7-[3-(4-benzylpiperazin-1-yl)-propoxy]-2-oxo-1,2-dihydroquinoline of the formula

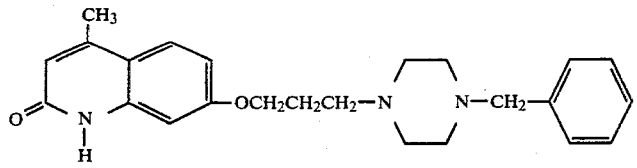

6. A compound or salt thereof according to claim 1, wherein such compound is 3-n-butyl-4-methyl-7-{3-[4-(4-chlorobenzyl)-piperazin-1-yl]-propoxy}-2-oxo-1,2-dihydroquinoline of the formula

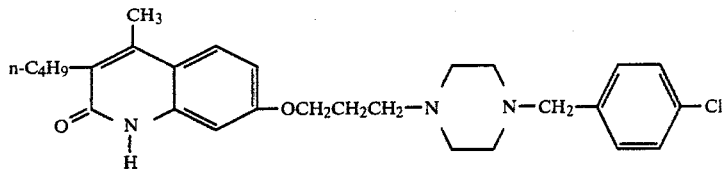

7. An anti-allergic and anti-hypertensive composition of matter comprising an anti-allergically anti-hypertensive effective amount of a compound or salt according to claim 1 in admixture with a pharmacologically acceptable diluent.

8. A method of reducing an allergic or hypertensive condition in a patient which comprises administering to such patient an anti-allergically or anti-hypertensive effective amount of a compound or salt according to claim 1.

9. The method according to claim 8, wherein said compound is 4-methyl-7-{3-[4-(4-chlorobenzyl)-piperazin-1-yl]-propoxy}-2-oxo-1,2-dihydroquinoline,
4-methyl-6-{3-[4-(4-chlorobenzyl)-piperazin-1-yl]-propoxy}-2-oxo-1,2-dihydroquinoline,
4-methyl-7-[3-(4-benzylpiperazin-1-yl)-propoxy]-2-oxo-1,2-dihydroquinoline, or
3-n-butyl-4-methyl-7-{3-[4-(4-chlorobenzyl)-piperazin-1-yl]-propoxy}-2-oxo-1,2-dihydroquinoline.

* * * * *

Disclaimer 4,234,585.—*Werner Winter*, Heppenheim; *Walter-Gunar Friebe*, Darmstadt; *Wolfgang Kampe*, Heddesheim; *Androniki Roesch*, Mannheim and *Otto-Henning Wilhelms*, Weinheim-Rittenweier, all of Fed. Rep. of Germany. 1,2-DIHYDROQUINOLINE-2-ONE DERIVATIVES. Patent dated Nov. 18, 1980. Disclaimer filed Mar. 21, 1983, by the assignee, *Boehringer Mannheim GmbH.*

Hereby enters this disclaimer to claims 1, 2, 7 and 8 of said patent.

[*Official Gazette January 3, 1984.*]

Notice of Adverse Decision in Interference

In Interference No. 100,864, involving Patent No. 4,234,585, W. Winter, W. G. Friebe, W. Kampe, A. Roesch and O. H. Wilhelms, 1, 2-DIHYDROQUINO-LINE-2-ONE DERIVATIVES, final judgment adverse to the patentees was rendered Dec. 11, 1985, as to claims 3, 4, 5, 6 & 9.

[*Official Gazette July 15, 1986.*]